United States Patent [19]

Grollier et al.

[11] Patent Number: 4,793,990
[45] Date of Patent: Dec. 27, 1988

[54] USE OF COFFEE BEAN OIL AS A SUN FILTER

[75] Inventors: Jean F. Grollier; Sophie Plessis, both of Paris, France

[73] Assignee: L'oreal, Paris, France

[21] Appl. No.: 458,638

[22] Filed: Jan. 17, 1983

Related U.S. Application Data

[63] Continuation of Ser. No. 249,823, Apr. 1, 1981, abandoned.

[30] Foreign Application Priority Data

Apr. 2, 1980 [LU] Luxembourg ............................ 82 323

[51] Int. Cl.$^4$ ........................ A61K 7/021; A61K 7/06; A61K 7/42; A61K 7/44
[52] U.S. Cl. .......................................... 424/59; 8/405; 424/DIG. 5; 424/47; 424/60; 424/61; 424/63; 424/64; 424/70; 424/74; 514/844; 514/845; 514/846; 514/847; 514/937; 514/944
[58] Field of Search ............................................ 429/59

[56] References Cited

U.S. PATENT DOCUMENTS

| | | | |
|---|---|---|---|
| 2,418,595 | 4/1947 | Brown | 424/59 |
| 2,853,423 | 9/1958 | La Via | 424/60 X |
| 2,880,140 | 3/1959 | de Navarre | 424/60 |
| 2,950,986 | 8/1960 | Bailey et al. | 424/60 X |
| 3,065,144 | 11/1962 | Kreps | 424/60 |
| 3,068,153 | 12/1962 | Morehouse | 424/60 |

FOREIGN PATENT DOCUMENTS

| | | | |
|---|---|---|---|
| 2199971 | 4/1974 | France | 424/59 |
| 2236515 | 2/1975 | France | 424/59 |
| 2383904 | 10/1978 | France | 424/59 |

OTHER PUBLICATIONS

Kaufmann, "Fette, Seifen, Anstrichmittel", 64, 206 (1962).
Tiscornia, "Rivista italinia sostanze grasse", 56, 283 (1979).

*Primary Examiner*—Dale R. Ore
*Attorney, Agent, or Firm*—Fleit, Jacobson, Cohn & Price

[57] ABSTRACT

A sun filter has been discovered which is coffee bean oil which can be obtained by extraction with an organic solvent from coffee grounds which are the residues from the extraction of water-soluble constituents from roasted coffees.

11 Claims, No Drawings

USE OF COFFEE BEAN OIL AS A SUN FILTER

This is a continuation of application Ser. No. 249,823, filed Apr. 1, 1981, now abandoned.

The present invention relates to the use of coffee bean oil as a sun filter, to the compositions in which this oil is present, and also to a process of protection against solar radiation in which coffee bean oil is employed.

It is known that light radiation between 280 and 400 nanometers (nm) makes it possible to tan the human epidermis, but that the zone between 280 and 320 nm, known by the name UV.B, causes erythema and skin burns, the severity of which increases rapidly with the exposure time. Thus, a good protective agent must have a high absorption capacity in the zone from 280 to 320 nm approximately, but it must transmit as much of the radiation as possible in the zone above 320 nm in order to offer the best conditions for browning without erythema and thus to allow the skin to develop its natural means of protection.

Attempts have therefore been made to delay as much as possible the appearance of solar erythema and its development into burns, whilst at the same time promoting natural browning.

In the past, it has been recommended to use, as the sun filter, a composition which is derived from coffee and which essentially comprises the water-extractable constituents and the constituents extracted with petroleum ether. However, these compositions exhibit the disadvantage of absorbing the ultraviolet rays in the whole wavelength range of ultraviolet radiation between 280 and 405 nm.

We have discovered, surprisingly, according to the present invention, that by using only coffee bean oil, which does not contain, in particular, all the water-soluble extracts of coffee, an agent is obtained which filters light selectively in the wavelength range from 280 to 320 nm, making it possible to brown the skin whilst at the same time avoiding solar erythema.

The agents used as sun filters must have a good resistance to external elements, that is to say they must be stable to light and heat and generally have a good substantivity towards the skin, so that they are not removed or degraded by perspiration, soft water or sea water.

They must also be non-toxic and non-irritant and have no harmful effects on the skin.

Finally, these agents must be easy to apply to the skin, so as to form an effective protective film. In particular, they must be capable of uniform distribution in cosmetic carriers suitable for forming a continuous film.

In this respect, the invention also overcomes or mitigates the disadvantages of the compositions formerly recommended as a sun filter, which contain all the soluble derivatives of coffee. In fact, although these compositions have in themselves certain properties of absorbing radiation in the whole of the ultraviolet spectrum, they are difficult to distribute over the skin and their appearance makes them generally rather unsuitable for cosmetic use.

Furthermore, it has already been proposed to use other oils extracted from natural products such as cucurbitaceae, rice bran and the like; although they possess a few absorptive properties towards ultraviolet radiation, these oils have the disadvantage of exhibiting an absorption peak which is a relatively long way from the radiation zone causing the maximum erythematous reaction of the skin.

The present invention thus provides coffee bean oil as a sun filter which is selective towards erythematogenous radiation having a wavelength from 280 to 320 nm and which permits browning in the nonerythematogenous radiation range from 320 to 400 nm.

The invention also provides cosmetic compositions in which coffee bean oil is present as the sun filter, and also to a process of protection against ultraviolet radiation in which coffee bean oil is applied.

The coffee bean oil used as a sun filter which is selective towards radiation having a wavelength of 280 to 320 nm is a lipid complex which can be obtained from coffee grounds, which are the residues from the extraction of the water-soluble constituents from roasted coffees.

The preparation of coffee bean oil from coffee grounds is well known and it is possible to use various techniques consisting, for example, in drying the moist grounds and extracting the coffee bean oil by means of an organic solvent. Numerous solvents can be used, for example hydrocarbons, such as, hexane, or chlorinated or fluorinated hydrocarbons. It is also possible to centrifuge the aqueous slurry of grounds in order to cause the coffee bean oil to separate out; the coffee bean oil is recovered in the upper phase. Other methods consist in rendering the aqueous slurry of grounds alkaline and then subjecting it to centrifugation, or in treating the grounds in water heated to the boil, and recovering the oil which separates out.

The analytical characteristics of coffee bean oil are not substantially influenced by the preparative treatments and they fall within a relatively narrow range.

Coffee bean oil essentially consists of about 75% of triglycerides and about 20% of fatty acid monoesters of two diterpene alcohols, namely caffestol and kahweol. It also contains phosphatides, sterol esters and also caffestol, kahweol and free fatty acids.

The coffee bean oil more particularly used according to the invention has essentially the following composition:

triglycerides of saturated or unsaturated $C_{14}$ to $C_{21}$ fatty acids: 74–78%
monoesters of caffestol and kahweol: 18–21%
phosphatides: 2–4%
fatty acid esters of sterols: 1 to 2%
free caffestol and kahweol: 1 to 2%

These percentages are expressed by weight, relative to the weight of the coffee bean oil.

The monoesters of caffestol and kahweol are essentially palmitates and linoleates.

For further details concerning the coffee bean oils which can be used according to the invention, reference should be made to the article by H. P. Kaufmann in "Fette, Seifen, Anstrichmittel" 64, 206 (1962), and to the article by Tiscornia in "Rivista italinia sostanze grasse" 56, 283 (1979).

The coffee bean oils which are more particularly preferred consist of coffee bean oil which has been deodorised by treatment with steam or in vacuo, in accordance with conventional techniques, decolourised coffee bean oil or coffee bean oil which has an enriched terpene fraction.

The enrichment in terpene fraction can be effected by conventional processes of molecular distillation. The enriched coffee bean oil generally has a triglyceride content of less than 70% and a caffestol and kahweol content of more than 2%. In this case, the coffee bean oil essentially consists of free caffestol or kahweol, monoesters of caffestol and kahweol, phosphatides and sterol esters.

We have discovered that the coffee bean oil enriched in this way has an improved protection index compared with the coffee bean oil as extracted by means of a solvent or any other process mentioned above.

The cosmetic compositions containing the coffee bean oil defined above as the sun filter can also contain other sun filters which are well known in the state of the art.

Coffee bean oil makes it possible to prepare sun filter compositions comprising a greasy phase, which consists totally or partially of the coffee bean oil, and an aqueous phase, which optionally contains a water-soluble sun filter, the emulsions produced in this way being either of the oil-in-water type or of the water-in-oil type.

The following may be mentioned in particular as water-soluble sun filters which can be used according to the invention: the benzylidene-camphor derivatives described in French Patents or French Patent Applications Nos. 2,199,971, 2,236,515 and 2,383,904 and more particularly 4-(2-oxobornylidene-3-methyl)-phenyltrimethylammonium methylsulphate, 4-(2-oxobornylidene-3-methyl)-benzenesulphonic acid, 2-methyl-5-(2-oxobornylidene-3-methyl)-benzenesulphonic acid and also the salts of 2-phenylbenzimidazole-5-sulphonic acid.

Another method of producing compositions according to the invention consists in strengthening the filtering action of the coffee bean oil by incorporating a liposoluble sun filter therein. It is thus possible to obtain high protection indices whilst at the same time using relatively smaller amounts of synthetic sun filter. This oil, strengthened in this way, can be incorporated into emulsions of which the aqueous phase can optionally contain a water-soluble filter.

Examples of lipophilic sun filters which may be mentioned are salicylic acid derivatives, such as 2-ethylhexyl salicylate and homomenthyl salicylate, cinnamic acid derivatives, such as ethylhexyl p-methoxycinnamate and 2-ethoxyethyl p-methoxycinnamate, para-aminobenzoic acid derivatives, such as amyl para-dimethylaminobenzoate, amyl para-aminobenzoate and 2-ethylhexyl para-dimethylaminobenzoate, benzophenone derivatives, such as 2-hydroxy-4-methoxybenzophenone and 2,2'-dihydroxy-4-methoxybenzophenone, camphor derivatives, such as benzylidene-camphor and 3-(4-methylbenzylidene)-camphor optionally associated with 4-isopropyldibenzoylmethane, and derivatives described in French Patent Application No. 2,383,904.

Finally, coffee bean oil can be used as the only carrier for filtering compositions, especially for the preparation of sun oils. In this case, it is possible, if appropriate, to introduce, for example, perfumes, liposoluble sun filters, such as those defined above, or, if appropriate, other filtering or nonfiltering vegetable oils, such as sesame oil, gourd oil, rapeseed oil, groundnut oil, wheatgerm oil, jojoba oil, maize oil, avocado oil, soya oil, grapeseed oil, sunflower seed oil and hazelnut oil.

We have found that such compositions have high protection indices towards UV B radiation.

The compositions according to the invention can be presented in the form of, for example, a solution, a lotion, an emulsion, a cream, a gel, a foam or a milk or in any other forms used in this field.

It is possible to add various cosmetic adjuvants thereto, such as thickeners, softeners, superfatting agents, emollients, humectants, anionic, cationic, nonionic or amphoteric surface-active agents, preservatives, anti-foam agents, colorants and/or pigments serving to colour the composition itself or the skin, perfumes and other ingredients normally used in cosmetics. The compositions can also be packaged in the form of an aerosol, in the presence of a propellant gas.

These compositions suitably contain coffee bean oil in an amount from 0.05 to 100% by weight.

Coffee bean oil can also be incorporated into treatment creams for the epidermis or into make-up products e.g. make-up foundations, lipsticks, nail varnishes, and tinted or non-tinted emulsions or creams for the skin.

Coffee bean oil can also be used in compositions containing constituents which are sensitive to ultraviolet radiation and in particular sensitive to radiation having a wavelength between 280 and 320 nm. In this case, the coffee bean oil essentially serves to protect the compositions against the degradation of these compounds.

Coffee bean oil can also be used in treatment compositions for the hair, such as shampoos, lotions and dyeing compositions, or in compositions intended for the care of the skin or nails, such as products for the bath, soaps and make-up products. The compositions can be presented in the form of, for example, dispersions, emulsions, creams or gels or in any form normally used in cosmetics. They can also be packaged in the form of an aerosol. In this case, the oil essentially serves as a carrier.

The following Examples further illustrate the present invention.

EXAMPLE 1

The following composition is prepared:
Self-emulsifiable glycerol monostearate: 6 g
Coffee bean oil: 30 g
Sorbitan monostearate polyoxyethyleneated with 60 mols of ethylene oxide: 2 g
Stearic acid: 2 g
Pure cetyl alcohol: 1.2 g
Propylene glycol: 2 g
Lanolin: 8 g
Triethanolamine: 0.1 g
Methyl para-hydroxybenzoate: 0.2 g
Perfume: 0.6 g
Water q.s.p.: 100 g The composition prepared in his way is in the form of a cream, making it possible to obtain a thin continuous film on the skin, and provides the latter with effective protection.

EXAMPLE 2

The following composition is prepared:
Mixture of cetyl/stearyl alcohol and oxyethyleneated cetyl/stearyl alcohol, sold under the name SINNOVAX A0 by Henkel: 6 g
Glycerol monostearate: 2 g
Coffee bean oil: 15 g
Rhodorsil oil 70047 V 300 (methylpolysiloxane) sold by Rhone Poulenc: 1.5 g
Cetyl alcohol: 1.5 g
Preservative: 0.2 g
Glycerol: 6 g
4-(2-Oxybornylidene-3-methyl)-phenyltrimethylammonium methylsulphate: 4 g
Perfume: 0.6 g Water q.s.p.: 100 g
The same results are observed as for Example 1.

EXAMPLE 3

The following composition is prepared:
Glycerol monostearate: 4 g
Cetyl/stearyl alcohol oxyethyleneated with 15 mols of ethylene oxide: 5 g
Lanolin: 3 g
Deodorised coffee bean oil: 15 g
2-Phenylbenzimidazole-5-sulphonic acid: 2.5 g
Triethanolamine: 1.3 g
Propylene glycol: 5 g
Methyl para-hydroxybenzoate: 0.2 g
Perfume: 0.6 g
Water q.s.p.: 100 g This composition is in the form of a milk which, when applied to the skin, gives a good protection against erythematous irradiation without preventing the browning radiation from passing through.

EXAMPLE 4

The following composition is prepared:
Mixture of cetyl/stearyl alcohol and cetyl/stearyl alcohol oxyethyleneated with 15 mols of ethylene oxide: 7 g
Glycerol monostearate: 2 g
Deodorised coffee bean oil: 15 g
Isopropyl myristate: 2.5 g
Cetyl alcohol: 1.5 g
3-(4-Methylbenzylidene)-camphor: 2.5 g
Kathon CG (mixture of 5-chloro-2-methylisothiazol-4-en-3-one, 2-methylisothiazol-4-en-3-one, magnesium chloride and calcium chloride, sold by Rohm and Haas), in an aqueous solution containing 1.5% of active ingredient: 0.2 g
Glycerol: 10 g
2-Phenylbenzimidazole-5-sulphonic acid: 2.5 g
Triethanolamine: 1.3 g
Perfume: 0.6 g
Water q.s.p.: 100 g

EXAMPLE 5

The following composition is prepared:
Glycerol monostearate: 6 g
Deodorised coffee bean oil: 25 g
Vaseline oil: 5 g
Sorbitan monostearate polyoxyethyleneated with 60 mols of ethylene oxide: 2 g
Stearic acid: 2 g
Cetyl alcohol: 1 g
Lanolin: 4 g
Mixture of 4-isopropylidibenzoylmethane and 3-(4-methylbenzylidene)-camphor: 5 g
Propylene glycol: 2 g
Triethanolamine: 0.1 g
Preservative: 0.2 g
Perfume: 0.5 g
Water q.s.p.: 100 g This compositon, which is in the form of a cream, makes it possible to obtain an effective screen for very sensitive skin.

EXAMPLE 6

Perfumed oil

Perfume: 0.5 g
Coffee bean oil q.s.p.: 100 g

A good protection of the skin against erythematous irradiation is obtained by virtue of this composition.

EXAMPLE 7

The following composition is prepared:
Benzylidene-camphor: 3 g
Perfume: 0.5 g
Coffee bean oil q.s.p.: 100 g

EXAMPLE 8

The following composition is prepared:
Sesame oil: 60 g
Perfume: 0.5 g
Coffee bean oil q.s.p.: 100 g

EXAMPLE 9

The following composition is prepared:
Coffee bean oil: 20 g
Gourd oil: 50 g
Perfume: 0.5 g
Sesame oil q.s.p.: 100 g

EXAMPLE 10

The following composition is prepared:
Rapeseed oil: 60 g
Perfume: 0.5 g
Coffee bean oil q.s.p.: 100 g The compositions of Examples 7 to 10 provide the skin with a good protection against UV B radiation.

They can also be applied to the hair during exposure to the sun.

EXAMPLE 11

The following composition is prepared:
2-Octyldodecanol sold under the name Eutanol G by Kenkel: 10 g
Magnesium stearate: 4 g
Hydrogenated lanolin: 1 g
Lanolin: 4 g
Beeswax: 5 g
Sorbitan sesquioleate sold under the name Arlacel 83 by Atlas: 4.5 g
Terpene-enriched coffee bean oil: 27 g
Propyl para-hydroxybenzoate: 0.1 g
Methyl para-hydroxybenzoate: 0.15 g
Perfume: 0.5 g
Water q.s.p.: 100 g When applied to the skin, this composition provides an effective protection.

We claim:

1. A sun filter composition, adapted for application to the human skin, which comprises a coffee extract consisting of a coffee bean oil which does not contain water soluble extracts, said composition being in the form of (1) an oil-in-water or water-in-oil emulsion containing said coffee bean oil, (2) a gel containing said coffee bean oil, or (3) an oil which is a mixture of said coffee bean oil and a vegetable oil other than coffee bean oil, wherein said coffee bean oil has a high absorption capacity to filter light selectively in the range of 280 to 320 nm and a low absorption capacity to filter light in the range above 320 nm.

2. A sun filter composition comprising an oil-in-water emulsion, a water-in-oil emulsion, or an oil containing coffee bean oil which does not contain water soluble extracts of coffee, said coffee bean oil being contained in the oil phase of the emulsion or the oil and said coffee bean oil having a high absorption capacity to filter light selectively in the range of 280 to 320 nm and a low absorption capacity of filter light in the range of above 320 nm, the oil also containing at least one oil soluble sun filter different from said coffee bean oil, perfume, at least one oil having sun filtering properties different from said coffee bean oil, or a mixture thereof.

3. The composition of claim 2 in which the coffee bean oil is deodorized coffee bean oil or coffee bean oil in which a terpene fraction of the coffee bean oil has been enriched.

4. The composition of claim 2 in which the coffee bean oil contains by weight about 74 to 78% triglycerides, about 18 to 21% monoesters of caffestol and kahweol, and 2 to 4% phosphatides, about 1 to 2% sterol esters, and about 1 to 2% free caffestol or kahweol.

5. The composition of claim 2 in which the composition also contains one or more sun filters in addition to the coffee bean oil.

6. The composition of claim 5 in which the one or more sun filters are water soluble sun filters.

7. The composition of claim 5 in which the one or more sun filters are liposoluble sun filters.

8. Solar composition according to claim 2 containing as a sun filter different from coffee bean oil a sum filter of the group comprising the benzilidene camphor derivatives, salicylic acid derivatives, cinnamic acid derivatives, para-aminobenzoic acid derivatives, benzophenone derivatives and dibenzoylmethane derivatives.

9. The composition of claim 2 in which the composition contains one or more thickeners, softeners, superfatting agents, emollients, humectants, anionic, cationic, non-ionic or amphoteric surface-active agents, preservatives, anti-foam agents, colorants, pigments or perfumes.

10. A process for protecting the skin against ultraviolet radiation having a wavelength of about 280 to 320 nm comprising applying to the skin to be protected a composition comprising an oil-in-water emulsion, a water-in-oil emulsion or an oil, containing coffee bean oil which does not contain water soluble extracts of coffee, the coffee bean oil being contained in the oil phase of the emulsion or the oil.

11. Sun filter composition in the form of an oil-in-water or water-in-oil emulsion containing coffee bean oil which does not contain water soluble extracts of coffee in the oil phase, in the form of a gel or in the form of an oil which is a mixture of coffee bean oil or with a vegetable oil other than coffee bean oil or with an oil soluble sun filter different from coffee bean oil or a mixture thereof, wherein the coffee bean oil has a high absorption capacity to filter light selectively in the range from 280 to 320 nm and a low absorption capacity to filter light in the range above 320 nm.

* * * * *